United States Patent [19]

Buckland

[11] Patent Number: 5,220,041
[45] Date of Patent: Jun. 15, 1993

[54] SULFONATE ESTER

[75] Inventor: Paul R. Buckland, Pittsford, N.Y.

[73] Assignee: Eastman Kodak Company, Rochester, N.Y.

[21] Appl. No.: 823,506

[22] Filed: Jan. 21, 1992

Related U.S. Application Data

[63] Continuation-in-part of Ser. No. 664,157, Mar. 4, 1991, abandoned.

[51] Int. Cl.$^5$ .................. C07D 307/06; C07C 309/09; C07C 309/66
[52] U.S. Cl. ..................... 549/493; 558/49; 558/50
[58] Field of Search ...................... 558/49, 50; 549/493

[56] References Cited

U.S. PATENT DOCUMENTS 3,271,451  9/1966  Tishler et al. ............... 260/570.8
3,536,721 10/1970  Soong et al. ................ 260/293.4
3,715,363  2/1973  Dickman ..................... 260/306

FOREIGN PATENT DOCUMENTS 372445  6/1990  European Pat. Off. .
11609   6/1965  Japan ........................ 558/49

OTHER PUBLICATIONS

Chem. Pharm. Bull., 38 (6) 1473-1478, Kita et al., "Chemistry of O-Silylated Ketene Acetals:", 1990.

Primary Examiner—Marianne M. Cintins
Assistant Examiner—Margaret Page

[57] ABSTRACT

Omega-alkanesulfonoxyalkanamides which are useful as alkylating agents are provided. Such alkylating agents are particularly useful for appending groups of the formula —Y—CONR$^8$R$^9$ wherein Y is selected from the group consisting of unsubstituted or substituted trimethylene, tetramethylene, or pentamethylene; and R$^8$ and R$^9$ are hydrogen or various hydrocarbyl radicals onto electrophilic sulfur, oxygen or nitrogen moieties.

2 Claims, No Drawings

SULFONATE ESTER

CROSS REFERENCE TO RELATED APPLICATIONS

This application is a continuation in part of U.S. application Ser. No. 07/664,157 filed Mar. 4, 1991 now abandoned.

FIELD OF THE INVENTION

This invention belongs to the field of synthetic organic chemistry. More particularly, this application relates to sulfonate esters as alkylating agents.

BACKGROUND OF THE INVENTION

The synthesis and use of substituted imidazoles in pharmaceutical preparations useful in treating atherosclerosis and in lowering serum cholesterol is known. For example, EP 0 372 445 A1 discloses an antihypercholesterolemic agent having the formula:

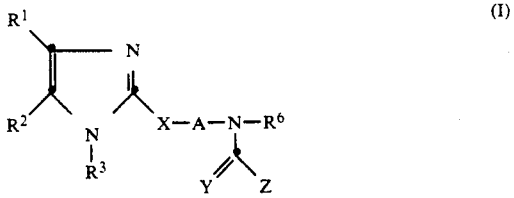

wherein
- $R^1$ and $R^2$ are various hydrocarbyl or heteroaryl groups;
- $R^3$ is hydrogen or various hydrocarbyl groups;
- X is $S(O)_r$, O, $NR^5$, or $CH_2$, wherein r is 0-2 and $R^5$ is H, $C_1$-$C_6$ alkyl, or benzyl;
- A is $C_2$-$C_{10}$ alkyl, $C_3$-$C_{10}$ branched alkyl, $C_3$-$C_{10}$ alkenyl, or $C_3$-$C_{10}$ alkynyl;
- Y is O, S, or $H_2$;
- Z is $NHR^4$, $OR^4$, or $R^4$, wherein $R^4$ is various substituted and unsubstituted hydrocarbyl groups; and
- $R^6$ is hydrogen or various substituted and unsubstituted hydrocarbyl groups. (See EP 0 372 445 A1, pp. 5-7).

Scheme 1, disclosed on page 9 of the European application, utilizes an imidazole as the starting compound and produces the antihypercholesterolemic agent as follows:

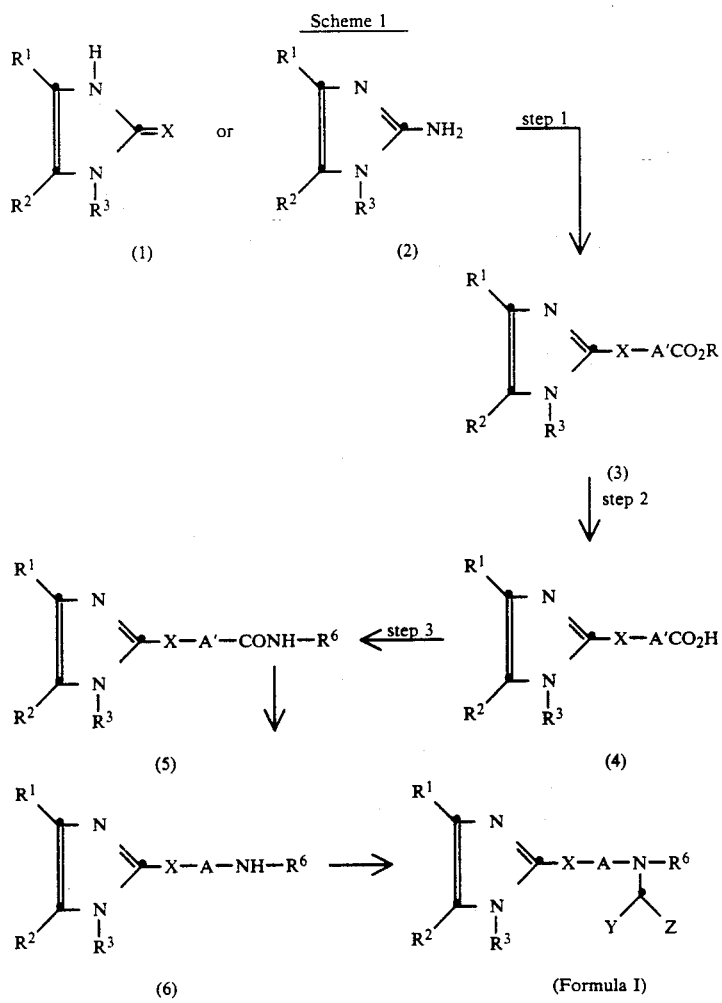

wherein the substituents are as defined for Formula (I).

According to the scheme presented above, the esters of Formula (3) are hydrolyzed to the corresponding carboxylic acids of Formula (4) by methods well known in the art. The amides of Formula (5) are prepared by coupling the carboxylic acids of Formula (4) with a primary amine by amide bond forming reactions known in the art.

The problem is that the process represented by this reaction scheme is expensive because it is protracted and requires expensive omega haloalkanoates such as ethyl 5-bromopentanoate (step 1). Furthermore, the use of such omega haloalkanoates at the outset of a multi-step synthesis increases the cost disadvantage of this process. A further disadvantage to the use of omega haloalkanoates is that many are lachrymators and/or irritants. Yet another disadvantage is that step 3 requires expensive dehydrating agents or requires two reaction steps via the acid chloride. Finally, as shown in the examples of the European application, the overall yield of the compound of Formula (5) is only modest.

This European application also describes an alternative reaction (Scheme 4) for preparing the amides of Formula (5) which in turn are used to prepare compounds of Formula (I). Alternative Scheme 4 is represented in the European application (p. 11) as follows:

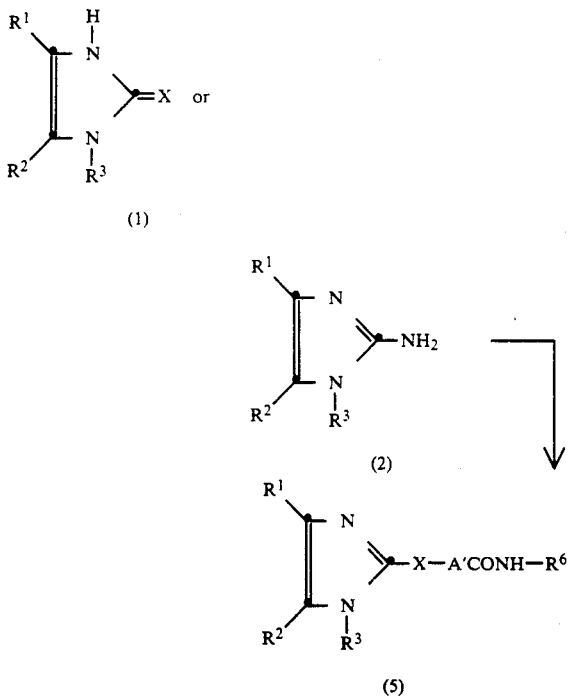

wherein the substituents are as described above.

Without teaching how, EP 0 372 445 A1 suggests that alternatively the amides of Formula (5) can be prepared by the alkylation of Formula (1) or (2) with compounds of the formula:

M-(A')CONH$^6$   (II)

wherein M is a halogen or tosylate group; A' is a moiety having one less methylene group than A (as described for Formula (I)); and R$^6$ is as defined for Formula (I).

The European application merely alludes to this alternative alkylation step. It does not teach the preparation of M (A')CONHR$^6$ (designated compound II), nor does it indicate the efficiency, yield, or economy of the suggested alkylating compound II, M (A')CONHR$^6$.

We have found that tosylate esters of this formula (wherein M=tosylate group) decompose at ambient temperatures or more rapidly on heating. The comparative example herein shows that formation of the suggested tosylate esters of compound II occurs only slowly at room temperature. During the slow reaction at room temperature, the product begins to decompose even before the reaction is complete, thus yielding less than optimum amounts of product.

We have also found that the tosylate esters are difficult to purify and difficult to solidify. On the other hand, although the halogen compounds of Formula II (wherein M=halogen) can be derived from omega haloalkanoyl chlorides, these materials are expensive to produce and many are lachrymators. Furthermore, the chloro analogs alkylate only slowly and incompletely.

What is needed to produce a high overall yield of compounds of Formula (5) are reactive alkylating agents which are themselves rapidly formed and are capable of being obtained pure from inexpensive and readily available starting materials.

SUMMARY OF THE INVENTION

I have developed an alkylating agent which solves the above identified problems. The alkylating agent claimed herein is used in copending and commonly assigned application U.S. Ser. No. 07/663,525, incorporated herein by reference, filed on Mar. 4, 1991 by Paul Buckland entitled "Preparation of Omega Substituted Alkanamides". The related application employs a sulfonyl ester in one step (step c) of the process of preparing substituted alkanamides.

More specifically, in accordance with one aspect of the invention, there are provided the compounds referred to herein as omega alkanesulfonoxyalkanamides (see Formula V below).

An advantageous feature of these compounds is that they can be made from lactones which are readily available, inexpensive, non toxic, and capable of being rapidly transformed in high yield to omega hydroxy alkanamides.

Another advantageous feature of these compounds is that in contrast to the tosylates, they are formed rapidly and in high yield at low to ambient temperatures. Furthermore, the omega alkanesulfonoxy alkanamides can be obtained in pure form without difficulty, in contrast to the tosylates, and are excellent alkylating agents for the preparation of compounds like Formula (5) above.

Another advantage of this invention is that it avoids the use of lachrymatory materials.

Yet another advantageous feature of the invention is that the omega alkanesulfonoxyalkanamides are provided conveniently and in high overall yield.

Advantageous features other than those noted hereinabove will become apparent upon reference to the following Description of the Preferred Embodiments.

DESCRIPTION OF THE PREFERRED EMBODIMENTS

The compounds of the present invention are useful, for example, in a process for the preparation of compounds like Formula (5) above which are used in preparing agents for the treatment of atherosclerosis and for lowering high serum cholesterol. The preparation process comprises two steps as follows: step (a):

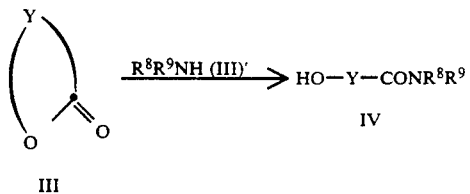

step (b):

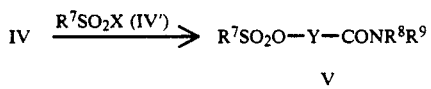

wherein
- (III) is a 5, 6, or 7 membered ring lactone such as delta valerolactone,
- (III') is an amine,
- (IV) is an omega hydroxyalkanamide,
- (IV') is an alkanesulfonic acid halide or anhydride,
- (V) is an omega-alkanesulfonoxyalkanamide,
- $R^7$ is selected from the group consisting of substituted or unsubstituted lower alkyls of 1-4 carbon atoms such as methyl, trifluoromethyl, ethyl, propyl, isopropyl.
- $R^8$ and $R^9$ each independently represents hydrogen, alkyl, alkenyl, cyclic alkyl, cyclic alkenyl, phenyl optionally substituted with 1 to 3 groups selected from $C_1$-$C_4$ alkyl or alkoxy, F, Br, Cl, OH, CN, $CO_2H$, $CF_3$, $NO_2$, $C_1$-$C_4$ carboalkoxy, $NR^{10}R^{10}$, or $NCOR^{11}$, benzyl optionally substituted with 1 to 3 groups selected from $C_1$-$C_4$ alkyl or alkoxy, F, Br, Cl, OH, CN, $CO_2H$, $CF_3$, $NO_2$, $C_1$-$C_4$ carboalkoxy, $NR^{10}R^{10}$ or $NCOR^{11}$, furfuryl, alkoxyalkyl and cyclic alkyl ethers with the proviso that $R^8$ and $R^9$ cannot both be aromatic. The term "cyclic alkyl" means a radical such as cyclohexyl which may be attached at the $R^8$ and/or $R^9$ position.
- $R^{10}$ is selected independently from $C_1$ to $C_4$ alkyl.
- $R^{11}$ is selected independently from H or $C_1$ to $C_4$ alkyl.
- Y is selected from the group consisting of unsubstituted or substituted trimethylene, tetramethylene or pentamethylene, exemplary substituents being divalent lower alkyl groups such as methylene, ethylene, propylene or butylene.
- X is selected from the group consisting of F, Cl, Br, $OSO_2R$.

The term "aromatic" as used herein refers to a group such as phenyl or napthyl.

The term "omega", as used herein, refers to the terminal or highest number position. It can be the 4, 5, or 6 position regardless of whether there are alkyl substituents at that same position.

In a broader sense, the alkylating agents of the present invention are useful in alkylating oxygen, nitrogen, or sulfur functionalities that are electrophilic in character, thereby inserting a group of the formula —Y—$CONR^8R^9$ where desired.

More specifically, the omega-alkanesulfonoxyalkanamides are produced by:

(a) adding a 5 to 7 membered ring lactone to an amine to produce an omega hydroxyalkanamide; and (b) condensing the omega hydroxyalkanamide of step (a) with an alkanesulfonic acid halide or anhydride to produce the omega-alkanesulfonoxyalkanamide.

More specifically, the omega-alkanesulfonoxyalkanamide is produced as follows:

Step (a): Addition reaction to prepare omega hydroxyalkanamide

A lactone is reacted with an amine to produce an omega hydroxyalkanamide. Preferably, the lactone has 5, 6, or 7 carbon atoms because these lactones are the most readily available and least expensive.

The following lactones are among those which would be useful in this reaction:gamma butyrolactone, gamma valerolactone, delta-valerolactone, gamma caprolactone, epsilon caprolactone.

Useful amines include n-heptylamine as well as other aliphatic primary and secondary amines.

The lactone and amine are made to react without a solvent as, unexpectedly, we have obtained a better yield in 3 to 6 hours under these conditions. The reaction takes place slowly at room temperature or more rapidly at elevated temperatures of about 40°-150° C., preferably 80°-110° C. The resulting omega hydroxy alkanamide may be recovered after crystallization as a solid or, to save time and for greater convenience, it may be reacted in situ during step (b).

Step (b): Condensation reaction to prepare omega-alkanesulfonoxyalkanamide

The hydroxyalkanamide resulting from step (a) is condensed with a small excess (about 5 to 10%) of methanesulfonic acid halide or anhydride in the presence of a small excess (about 10 to 20%) of an acid scavenger, for example, a tertiary amine such as triethylamine and the like. Suitable solvents are dichloromethane, methyl ethyl ketone, tetrahydrofuran, ethyl acetate and N,N-dimethylformamide. An inexpensive and readily available sulfonyl halide such as methane sulfonyl chloride is preferred. The reaction is carried out preferably between 10° C. and room temperature. The resulting omega-alkanesulfonoxyalkanamide is recovered after crystallization as a solid or reacted in situ in step (c).

Unexpectedly, the omega-alkanesulfonoxyalkanamide formed as an intermediate in the presently claimed process, can be readily recovered as a white solid with a 92% yield. This result is unexpected in view of our finding that the yield of the tosyl ester is only 76% and the product is difficult to purify. (See Comparative Example).

The following examples are given for purposes of illustrating the present invention and should not be construed as limiting the invention.

EXAMPLE 1- PREPARATION OF N-HEPTYL-5-METHANESULFONOXYPENTANAMIDE

Step (a): Preparation of N-Heptyl-5-hydroxypentanamide

Delta valerolactone (40 g, 0.4 mole) was added dropwise with stirring to n heptylamine (50.6 g, 0.44 mole) so that the temperature of the mixture was maintained at 85° to 90° C. Heat was applied and the temperature raised to 110° C. over 20 minutes after which the temperature was maintained at 110° to 115° C. for a further 6 hours (after 3 hours N.M.R. indicated that the reaction was 90 to 95% complete). Toluene (200 ml, 173 g) was added and the solution cooled to 0° C. with stirring. After 1 hour at 0° C., the solid was collected and washed successively with ice cold toluene (50 ml, 43 g) and n-heptane (50 ml, 34 g). The material was dried at room temperature overnight to give the product. (81.6 g (95% yield) m.p. 53° to 54° C.).

The reaction is represented as follows:

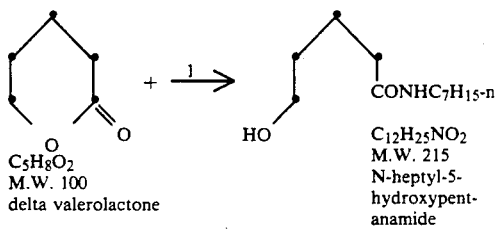

O
$C_5H_8O_2$
M.W. 100
delta valerolactone

HO
$C_{12}H_{25}NO_2$
M.W. 215
N-heptyl-5-hydroxypentanamide

1. N-heptylamine. Heat at 110 to 115 °C. for 6 hours.

Step (b): Preparation of N-heptyl-5-methanesulfonoxypentanamide

Dichloromethane (70 ml, 93 g) was added to a 4 necked 500 ml flask (condenser/drying tube, dropping funnel, thermometer, overhead stirrer) containing N-heptyl-5-hydroxypentanamide (32.25 g, 0.15 mole). Cooling occurred as the solid partially dissolved. Methanesulfonyl chloride (18.0 g, 0.1575 mole, 5% excess) was added and stirring continued at 15° C. for 30 minutes during which most of the solid dissolved. Cooling below 15° C. at this stage is not recommended because a thick slurry is produced due to recrystallization of the starting material. Dropwise addition over 1 hour, of a mixture of triethylamine (16.66 g, 0.165 mole, 10% excess) and dichloromethane (30 ml, 40 g) was commenced with cooling, so that the temperature remained at 13° to 16° C. throughout the addition. Shortly after (about 10 minutes), the addition was complete, t.l.c. (ethyl acetate, iodine/warm plate) indicated absence of starting material. After a further 1 hour, the mixture was stirred rapidly with cold 10° C. water (50 ml) for 1 minute. The layers were allowed to separate out over a further 5 minutes and the top aqueous layer (50 ml) carefully siphoned off and discarded. The washing procedure was repeated using cold (10° C.) 15% sodium chloride solution (40 ml) removing the top layer (35 ml). Finally the mixture was again washed with cold 15% sodium chloride solution (40 ml), this time running off the bottom dichloromethane layer into a 500 ml flask containing sodium sulfate (35 g) After stirring for 15 minutes at 15° C., the mixture was filtered through anhydrous sodium sulfate (35 g) and the residue washed with dichloromethane (50 ml, 66 g). The combined filtrates were evaporated below 20° C. at reduced pressure until crystallization began, to give a semi solid (94 g). n Heptane (100 ml, 68 g) was added and the mixture gradually cooled to 0° C. After stirring at 0° C. for 1 hour, the solid (47 g) was collected, washed with n-heptane (25 ml, 17 g) and dried at room temperature to give the product 40.7 g (92% yield) as a white solid, m.p. 63° to 64° C.

The reaction is represented as follows:

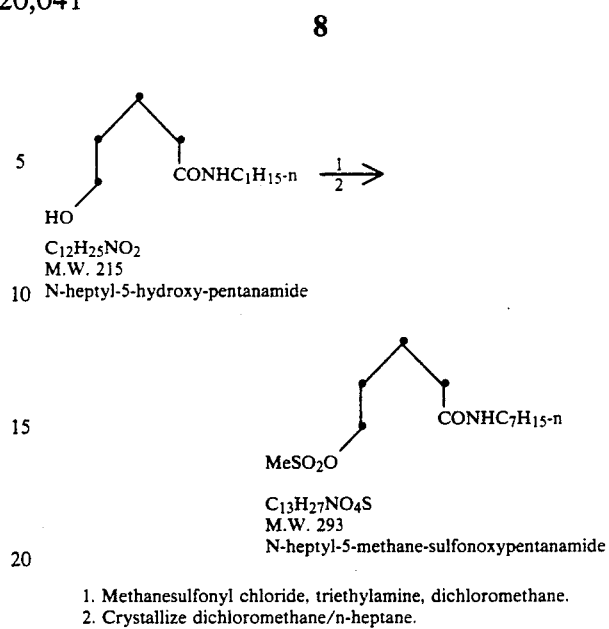

HO
$C_{12}H_{25}NO_2$
M.W. 215
N-heptyl-5-hydroxy-pentanamide

MeSO$_2$O
$C_{13}H_{27}NO_4S$
M.W. 293
N-heptyl-5-methane-sulfonoxypentanamide

1. Methanesulfonyl chloride, triethylamine, dichloromethane.
2. Crystallize dichloromethane/n-heptane.

COMPARATIVE EXAMPLE: PREPARATION OF N-HEPTYL-5-TOSYLOXYPENTANAMIDE

N-heptyl-5-hydroxypentanamide (3.23 g, 0.015 mole) and tosyl chloride (3.0 g, 0.1575 mole) were dissolved at room temperature in dichloromethane (10 ml). Cooling occurred as the solids dissolved. When complete solution was obtained (10 minutes), triethylamine (1.66 g, 0.0165 mole) was added dropwise at 16° C. No exotherm occurred. The temperature was maintained at 15° to 17° C. for a further 2 hours. The mixture was then washed successively with ice cold water (2×5 ml) and finally with saturated sodium chloride solution (5 ml). The organic solution was dried with sodium and magnesium sulfates and the solvent removed at room temperature to give a yellow oil 6.2 g. An N.M.R. spectrum indicated a 76% conversion of alcohol to sulfonate ester (product:alcohol 3.2:1). The oil did not crystallize at ambient temperatures but crystallized at −20° C. from toluene (10 ml) and n-heptane (5 ml) to give a solid 2.8 g which was still contaminated with unreacted alcohol (product:alcohol 2.8:1). This crude material was readily soluble in all common organic solvents except alkanes.

Despite the use of excess tosyl chloride, the initial 76% yield of sulfonate ester did not improve. Very little if any further conversion of alcohol occurred at longer reaction times up to 48 hours. After 48 hours N.M.R. showed unreacted alcohol still present and also confirmed that substantial decomposition of the product occurs on keeping in solution at ambient temperatures.

The reaction is represented as follows:

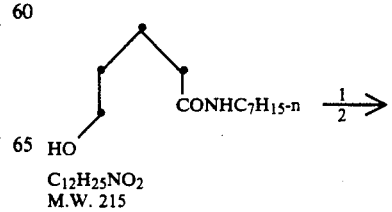

HO
$C_{12}H_{25}NO_2$
M.W. 215

-continued

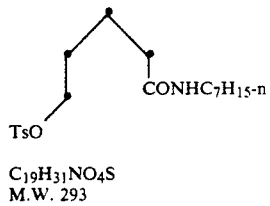

$C_{19}H_{31}NO_4S$
M.W. 293

1. Tosyl chloride, triethylamine, dichloromethane.
2. Crystallize from toluene/n-heptane.

The invention has been described in detail with particular reference to preferred embodiments thereof, but it will be understood that variations and modifications can be effected within the spirit and scope of the invention.

I claim:

1. Compounds having the formula:

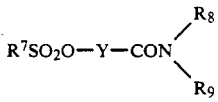

wherein $R^7$ is selected from the group consisting of methyl, trifluoromethyl, ethyl, propyl, isopropyl, and butyl, $R^8$ and $R^9$ each independently represents hydrogen; alkyl; alkenyl; cyclic alkyl; cyclic alkenyl; phenyl optionally substituted with 1 to 3 groups selected from $C_1-C_4$ alkyl or alkoxy, F, Br, Cl, OH, CN, $CO_2H$, $CF_3$, $NO_2$, $C_1-C_4$ carboalkoxy, $NR^7R^8$, or $NCOR^7$, benzyl optionally substituted with 1 to 3 groups selected from $C_1-C_4$ alkyl or alkoxy, F, Br, Cl, OH, CN, $CO_2H$, $CF_3$, $NO_2$, $C_1-C_4$ carboalkoxy, $NR^{10}R^{10}$ or $NCOR^{11}$; furfuryl; alkoxyalkyl; and cyclic alkyl ethers; with the proviso that $R^8$ and $R^9$ cannot both be aromatic, $R^{10}$ is selected independently from $C_1$ to $C_4$ alkyl, $R^{11}$ is selected independently from H or $C_1$ to $C_4$ alkyl, Y is a group of the formula $-CH_2CH_2CH_2CH_2-$.

2. N-heptyl-5-methanesulfonyloxypentanamide.

* * * * *